United States Patent [19]

Ginsburg

[11] Patent Number: 6,033,383

[45] Date of Patent: Mar. 7, 2000

[54] TEMPERATURE REGULATING CATHETER AND METHODS

[76] Inventor: Robert Ginsburg, 5100 S. Steele St., Greenwood Village, Colo. 80121

[21] Appl. No.: 08/769,931

[22] Filed: Dec. 19, 1996

[51] Int. Cl.[7] .................................................. A61F 7/12
[52] U.S. Cl. ........................ 604/113; 604/247; 604/508; 607/105
[58] Field of Search .............................. 604/49, 113, 114, 604/264, 280, 247; 607/96, 104–107

[56] References Cited

U.S. PATENT DOCUMENTS

| | | | |
|---|---|---|---|
| 2,308,484 | 1/1943 | Auzin et al. | 604/103 |
| 3,425,419 | 2/1969 | Dato | 607/113 |
| 3,726,283 | 4/1973 | Dye et al. | 604/247 |
| 3,788,328 | 1/1974 | Alley et al. | 604/178 |
| 3,995,617 | 12/1976 | Watkins et al. | 604/247 |
| 4,014,317 | 3/1977 | Bruno | 604/247 |
| 4,038,519 | 7/1977 | Foucras | 219/301 |
| 4,111,209 | 9/1978 | Wolvek et al. | 128/400 |
| 4,246,932 | 1/1981 | Raines | 137/512 |
| 4,298,006 | 11/1981 | Parks | 607/106 |
| 4,378,797 | 4/1983 | Osterholm | 604/24 |
| 4,445,500 | 5/1984 | Osterholm | 128/1 |
| 4,445,886 | 5/1984 | Osterholm | 604/28 |
| 4,470,407 | 9/1984 | Hussein | 128/6 |
| 4,540,402 | 9/1985 | Aigner | 604/44 |
| 4,661,094 | 4/1987 | Simpson | 604/53 |
| 4,662,383 | 5/1987 | Sogawa et al. | 128/784 |
| 4,672,962 | 6/1987 | Hershenson | 128/303 |
| 4,686,085 | 8/1987 | Osterholm | 422/45 |
| 4,701,166 | 10/1987 | Groshong et al. | 604/247 |
| 4,705,501 | 11/1987 | Wigners et al. | 604/43 |
| 4,748,979 | 6/1988 | Hershenson | 128/303.1 |
| 4,750,493 | 6/1988 | Brader | 128/380 |
| 4,754,752 | 7/1988 | Ginsburg et al. | 128/303 |
| 4,769,005 | 9/1988 | Ginsburg et al. | 604/53 |
| 4,804,358 | 2/1989 | Karcher et al. | 600/17 |
| 4,819,655 | 4/1989 | Webler | 128/713 |
| 4,840,617 | 6/1989 | Osterholm | 604/174 |

(List continued on next page.)

FOREIGN PATENT DOCUMENTS

WO 91/05528  2/1991  WIPO ............................... A61F 7/12

OTHER PUBLICATIONS

Long, R., "Regional Cranial Hypothermia in the Prevention of Cerebral Ischemic Damage During Carotid Occlusion", *Review of Surgery*, vol. 23, No. 3, May 1966, pp. 226–228.

White, R. et al., "Profound selective cooling and ischemia of primate brain without pump or oxygenator", Surgery, vol. 66, No. 1, Jul. 1969, pp. 224–232.

Weale, F.E., "The Aneroid Manometer in Peripheral Arterial Surgery", *The British Journal of Surgery*, vol. 56, No. 8, Aug. 1969, pp. 612–631.

Negrin, Jr., J., "The Hypothermostat: An Instrument to Obtain Local Hypothermia of the Brain or Spinal Cord", *International Surgery*, Sec. 1, vol. 54, No. 2, Aug. 1970, pp. 93–106.

Safar, P., "Resuscitation after global brain ischemia–anoxia", *Crit. Care Med.*, vol. 6, No. 4, (1978), pp. 215–227.

Ping, F. et al., "Protection of the Brain from Hypoxia: A Review", *Canad. Anaesth. Soc. J.*, vol. 25, No. 6, Nov. 1978, pp. 468–473.

(List continued on next page.)

*Primary Examiner*—Corrine McDermott
*Attorney, Agent, or Firm*—Stout, Uxa Buyan & Mullins, LLP

[57] ABSTRACT

The invention provides methods and apparatus for regulating the temperature of a liquid medium while the liquid medium is within a patient. According to one exemplary method, a catheter is provided having a catheter body with a proximal end and a distal end. At least one lumen extends between the proximal end and distal end, and an internal temperature altering region is near the distal end. The catheter is introduced into a body structure until the temperature altering region is near a target area within the body structure. A liquid medium is introduced into the lumen so that the temperature of the liquid medium may be altered while passing through the temperature altering region.

32 Claims, 5 Drawing Sheets

U.S. PATENT DOCUMENTS

| | | | |
|---|---|---|---|
| 4,857,054 | 8/1989 | Helfer | 604/102 |
| 4,892,095 | 1/1990 | Nakhgevany | 128/207.1 |
| 4,892,519 | 1/1990 | Songer et al. | 604/96 |
| 4,899,741 | 2/1990 | Bentley et al. | 606/27 |
| 4,909,252 | 3/1990 | Goldberger | 606/194 |
| 4,920,963 | 5/1990 | Brader | 128/402 |
| 4,941,475 | 7/1990 | Williams et al. | 128/692 |
| 4,976,691 | 12/1990 | Sahota | 604/96 |
| 4,995,863 | 2/1991 | Nichols et al. | 604/247 |
| 5,019,075 | 5/1991 | Spears et al. | 607/113 |
| 5,030,210 | 7/1991 | Alchas | 604/247 |
| 5,041,089 | 8/1991 | Mueller et al. | 606/28 |
| 5,092,841 | 3/1992 | Spears | 604/96 |
| 5,106,360 | 4/1992 | Ishiwara et al. | 600/2 |
| 5,112,301 | 5/1992 | Fenton, Jr. et al. | 604/30 |
| 5,147,385 | 9/1992 | Beck et al. | 623/1 |
| 5,149,321 | 9/1992 | Klatz et al. | 604/52 |
| 5,151,100 | 9/1992 | Abele et al. | 606/28 |
| 5,180,364 | 1/1993 | Ginsburg | 604/280 |
| 5,191,883 | 3/1993 | Lennox et al. | 607/113 |
| 5,196,024 | 3/1993 | Barath | 606/194 |
| 5,211,631 | 5/1993 | Sheaff | 606/194 |
| 5,234,405 | 8/1993 | Klatz et al. | 604/24 |
| 5,248,312 | 9/1993 | Langberg | 607/113 |
| 5,250,070 | 10/1993 | Parodi | 606/194 |
| 5,257,977 | 11/1993 | Eshel | 604/113 |
| 5,261,399 | 11/1993 | Klatz et al. | 607/104 |
| 5,269,758 | 12/1993 | Taheri | 604/96 |
| 5,342,301 | 8/1994 | Saab | 604/96 |
| 5,368,591 | 11/1994 | Lennox et al. | 606/27 |
| 5,383,856 | 1/1995 | Bersin | 604/103 |
| 5,395,314 | 3/1995 | Klatz et al. | 604/24 |
| 5,403,281 | 4/1995 | O'Neill et al. | 604/113 |
| 5,437,673 | 8/1995 | Baust et al. | 606/23 |
| 5,486,208 | 1/1996 | Ginsburg | 607/106 |
| 5,531,776 | 7/1996 | Ward et al. | 607/105 |
| 5,624,392 | 4/1997 | Saab | 604/43 |
| 5,653,692 | 8/1997 | Masterson et al. | 604/113 |

OTHER PUBLICATIONS

Safar, P., "Dynamics of Brian Resuscitation After Ischemic Anoxia", *Hospital Practice*, Feb. 1981, pp. 67–72.

Gisvold, S. et al., "Multifaceted Therapy After Global Brain Ischemia in Monkeys", *Stroke*, vol. 15, No. 5, Sep. 1984, pp. 803–812.

Leonov, Y. et al., "Mild Cerebral Hypothermia during and after Cardiac Arrest Improves Neurologic Outcome in Dogs", *Journal of Cerebral Blood Flow and Metabolism*, vol. 10, (1990), pp. 57–70.

Minamisawa, H. et al., "The Effect of Mild Hyperthermia and Hypothermia on Brain Damage Following 5, 10 and 15 Minutes of Forebrain Ischemia", American Neurological Association, (1990), pp. 26–33.

Tisherman, S. et al. "Therapeutic Deep Hypothermic Circulatory Arrest in Dogs: A Resuscitation Modality for Hemorrahagic Shock with 'Irreparable' Injury", *The Journal of Trauma*, vol. 30, No. 7, Jul. 1990, pp. 836–847.

Tisherman, S. et al., "Deep Hypothermic Circulatory Arrest Induced During Hemorrhagic Shock in Dogs: Preliminary Systemic and Cerebral Metabolism Studies", Current Surgery, Sep. 1990, pp. 327–330.

Leonov, Y. et al., "Moderate Hypothermia After Cardiac Arrest of 17 Minutes in Dogs: Effect on Cerebral and Cardiac Outcome", *Stroke*, vol. 21, No. 11, Nov. 1990, pp. 1600–1606.

Sterz, F. et al., "Mild Hypothermic Cardiopulmonary Resuscitation Improves Outcome after Prolonged Cardiac Arrest in Dogs", *Critical Care Medicine*, vol. 19, No. 3, (1991), pp. 379–389.

Tisherman, S. et al., "Profound Hypothermia (<10° C.) Compared with Deep Hypothermia (15° C.) Improves Neurologic Outcome in Dogs After Two Hours' Circulatory Arrest Induced to Enable Resuscitative Surgery", *The Journal of Trauma*, vol. 31, No. 8, Aug. 1991, pp. 1051–1062.

Dietrich, W., "The Importance of Brain Temperature in Cerebral Injury", *Journal of Neurotrauma*, vol. 9, Suppl. 2, (1992), pp. S475–S485.

Ginsberg, M. et al., "Therapeutic Modulation of Brain Temperature: Relevance to Ischemic Brain Injury", *Cerebrovascular and Brain Metabolism Reviews*, vol. 4, No. 3, (1992), pp. 189–225.

Martinez–Arizala, A. et al., "Hypothermia in Spinal Cord Injury", *Journal of Neurotrauma*, vol. 9, Suppl. 2, (1992), pp. S497–S505.

Weinrauch, V. et al., "Beneficial Effect of mild Hypothermia and Detrimental Effect of Deep Hypothermia After Cardiac Arrest in Dogs", *Stroke*, vol. 23, No. 10, Oct. 1992, pp. 1454–1462.

Kuboyama, K. et al., "Delay in cooling negates the beneficial effect of mild resuscitative cerebral hypothermia after cardiac arrest in dogs: A prospective, randomized study", *Crit. Care Med.*, vol. 21, No. 9, (1993), pp. 1348–1358.

Maher, J. et al., "Hypothermia as a Potential Treatment for Cerebral Ischemia", *Cerebrovascular and Brain Metabolism Reviews*, vol. 5, No. 4, (1993), pp. 277–300.

Safar, P., "Cerebral Resuscitation After Cardiac Arrest: Research Initiatives and Future Directions", *Annals of Emergency Medicine*, vol. 22, No. 2, Part 2, Feb. 1993, pp. 324–389.

Oku, K. et al., "Mild Hypothermia After Cardiac Arrest in Dogs Does Not Affect Postarrest Multifocal Cerebral Hypoperfusion", *Stroke*, vol. 24, No. 10, Oct. 1993, pp. 1590–1597.

Kuboyama, K. et al., "Mild hypothermia after cardiac arrest in dogs does not affect postarrest cerebral oxygen uptake/ delivery mismatching", *Resuscitation*, vol. 27, (1994), pp. 231–244.

Laptook, A. et al., "Modest Hypothermia Provides Partial Neuroprotection for Ischemic Neonatal Brain", *Pediatric Research*, vol. 35, No. 4, (1994), pp. 436–442.

Salzano, Richard P. et al., "Regional Hypothermia of the Spinal Cord Protects Against Ischemic Injury During Thoracic Aortic Cross–Clamping", *The Society of Thoracic Surgeons*, vol. 57, (1994), pp. 65–71.

Onoe, M. et al., "The Effect of Pulsatile Perfusion on Cerebral Blood Flow During Profound Hypothermia with Total Circulatory Arrest", *Journal of Thoracic and Cardiovascular Surgery*, vol. 108, Jul. 1994, pp. 119–125.

Xiao, F. et al., "Peritoneal cooling for mild cerebral hypothermia after cardiac arrest in dogs", *Resuscitation*, vol. 30, (1995), pp. 51–59.

Sessler, D., "Deliberate Mild Hypothermia", *Journal of Neurosurgical Anesthesiology*, vol. 7, No. 1, Jan. 1995, pp. 38–46.

Capone, A. et al., "Complete Recovery after Normothermic Hemorrahagic Shock and Profound Hypothermic Circulatory Arrest of 60 Minutes in Dogs", *The Journal of Trauma: Injury, Infection and Critical Care*, vol. 40, No. 3, (1996), pp. 388–395.

Gisvold, S. et al., "Cerebral resuscitation from cardiac arrest: Treatment potentials", *Crit. Care Med.,* vol. 24, No. 2 (Suppl.), (1996), pp. S69–S80.

Kataoka, K. et al., "Ischemic Neuronal Damage: How Does Mild Hypothermia Modulate It?", *Molecular and Chemical Neuropathology,* vol. 28, (1996), pp. 191–195.

Safar, P. et al., "Selective brain cooling after cardiac arrest", *Crit. Care Med.,* (1996), vol. 24, No. 6, pp. 911–914.

Sterz, F. et al., "Mild Resuscitative Hypothermia and Outcome After Cardiopulmonary Resuscitation", *Journal of Neurosurgical Anesthesiology,* vol. 8, No. 1, (1996), pp. 88–96.

Wass, C. et al., "Hypothermia–associated Protection from Ischemic Brain injury: Implications for Patient Management", *International Anesthesiology Clinics: Topics in Neuroanesthesia,* vol. 34, No. 4, (1996), pp. 95–111.

Safar, P. et al., "Improved Cerebral Resuscitation From Cardiac Arrest in Dogs With Mild Hypothermia Plus Blood Flow Promotion", *Stroke,* vol. 27, No. 1, Jan. 1996, pp. 105–113.

Marion, D. et al., "Resuscitative hypothermia", *Crit. Care Med.,* vol. 24, No. 2 (Suppl.), Feb. 1996, pp. S81–S89.

Rosomoff, H. et al., "Resuscitation from severe brain trauma", *Crit. Care Med.,* vol. 24, No. 2 (Suppl.), Feb. 1996, pp. S48–S56.

Markarian, G. et al., "Mild Hypothermia: Therapeutic Window after Experimental Cerebral Ischemia", *Neurosurgery,* vol. 38, No. 3, Mar. 1996, pp. 542–551.

Hoffman, W. et al., "Effects of graded Hypothermia on Outcome from Brain Ischemia", *Neurological Research,* vol. 18, No. 2, Apr. 1996, pp. 185–189.

Schwartz, A. et al., "Isolated Cerebral Hypothermia by Single Carotid Artery Perfusion of Extracorporeally Cooled Blood in Baboons", *Neurosurgery,* vol. 39, No. 3, Sep. 1996, pp. 577–582.

Metz, C. et al., "Moderate Hypothermia in Patients with Severe Head Injury: Cerebral and Extracerebral Effects", *Journal of Neurosurgery,* vol. 85, No. 4, Oct. 1996, pp. 533–541.

Jessen, C. et al., "Intravascular Heat Exchanger for Conscious Goats", Pflugers Archiv European Journal of Physiology, vol. 368, (1977) pp. 263–265.

TEMPERATURE REGULATING CATHETER AND METHODS

BACKGROUND OF THE INVENTION

The present invention relates generally to the regulation of the temperature of a fluid that is to be delivered to a specific target location within a body structure. More particularly, the invention provides methods and apparatus for altering the temperature of a fluid that is to be delivered to the target location while the fluid is within the patient.

On many occasions, the temperature of a fluid within a patient needs to be regulated. For example, in some medical procedures, various fluids, such as solutes or drugs, are delivered to target locations within the body. The desired temperature of these fluids upon delivery may vastly differ from the storage temperature. In such cases, it is therefore desirable to heat or cool the fluid before it reaches the target location. Although possible to heat or cool the fluid outside of the patient, such a procedure can be cumbersome and require elaborate equipment.

As another example, fluids at various temperatures may be introduced to a target location within a patient to regulate the temperature of a localized area within a body structure. One particular application where the heating or cooling of a specific area within a body structure is desirable is in the field of neurosurgery. In many cases, it is desirable to cool a specific area within the brain prior to performing a surgical procedure.

As a further example, the temperature of body fluids may be regulated to control the patient's body temperature. The regulation of the patient's body temperature is particularly useful in treating patient's suffering from either hypothermia or hyperthermia.

Under ordinary circumstances, the thermal regulatory system of the human body maintains a near constant temperature of about 37° C. (98.6° F.). Heat lost to the environment is precisely balanced by heat produced within the body. Hypothermia is a condition of abnormally low body temperature. Hypothermia can be clinically defined as a core body temperature of 35° C. or less. Accidental hypothermia results when heat loss to the environment exceeds the body's ability to produce heat internally. Hypothermia may also occur in patients exposed to mild cold stress whose thermal regulatory ability has been lessened due to injury and illness.

Hypothermia of either type is a dangerous condition which can have serious medical consequences. In particular, hypothermia interferes with the ability of the heart to pump blood. Hypothermia may be fatal for this reason alone. Additionally, low body temperatures seriously interfere with the enzymatic reactions necessary for blood clotting. This sometimes results in bleeding that is difficult to control, even when normal clotting factor levels are present. These effects and other adverse consequences of hypothermia lead to drastically increased mortality rates both among victims of trauma and in patients undergoing surgery.

Hyperthermia is a condition of abnormally high body temperature and may result from exposure to a hot environment, overexertion, or fever. Body core temperatures can range from 38° C. to 41° C. due to fever and may be substantially higher in cases of exposure and overexertion. Like hypothermia, hyperthermia is a serious condition and can be fatal.

Simple methods for treating both hypothermia and hyperthermia have been known since early times. In the case of hypothermia, such methods include wrapping the patient in blankets, administering warm fluids by mouth, and immersing the patient in a warm water bath. To treat hyperthermia, some have proposed immersion of the patient in a cool water bath or the administration of cool fluids. However, such methods can have serious drawbacks and limited effectiveness.

One particular catheter structure which has been developed to treat a patient suffering from either hypothermia or hyperthermia is described in U.S. Pat. No. 5,486,208, the complete disclosure of which is herein incorporated by reference. Such a catheter has the ability to heat or cool a liquid that is circulated through a catheter body.

Although such a catheter has been shown to be generally effective in the treatment of both hypothermia and hyperthermia, some improvements are still desired. For example, it would be desirable if such a catheter were more versatile to allow for the temperature of various fluids introduced into the body to be regulated. In this manner, the temperature of an introduced fluid could be more closely controlled at the point of introduction. It would be further desirable if a catheter structure and methods were provided for regulating the temperature of a localized region within a body structure prior to performing a medical procedure on the body structure.

SUMMARY OF THE INVENTION

The invention provides methods and apparatus for regulating the temperature of a fluid while the fluid is within the patient. Such a fluid can include, for example, an externally introduced fluid, an internal body fluid, or both. To provide such features, the present invention in one exemplary embodiment provides a catheter comprising a catheter body having a proximal end and a distal end. At least one lumen defining a luminal wall extends between the proximal end and the distal end. A temperature altering mechanism is disposed within the catheter body which heats or cools the luminal wall to alter the temperature of a fluid passing through the lumen.

The temperature altering mechanism may comprise a heater or a cooler, and is preferably located at a temperature altering area. The temperature altering area may be located anywhere along the catheter body and in some embodiments will preferably be located near the distal end of the catheter. In another aspect, the temperature altering mechanism is preferably disposed near the luminal wall to heat or cool the luminal wall without substantial heating of an outer surface of the catheter body. In this manner, a fluid may be externally introduced into a patient through a proximal port and be heated or cooled at the temperature altering region without heating or cooling of the outer surface of the catheter body. In this way, when the fluid exits the distal end of the catheter body, the fluid will be within a desired temperature range so that only a particular location within the patient which is near the distal end of the catheter will be heated or cooled.

In one exemplary aspect, a plurality of orifices are disposed within the catheter body to permit a body fluid to flow through the orifices and into the lumen. As the body fluid passes through the temperature altering region, the temperature of the body fluid is altered. In this manner, the catheter is provided with the versatility of altering the temperature of an externally introduced fluid, an internal body fluid, or both. In a particular aspect, a one-way valve is associated with each orifice to prevent the body fluids from entering into the lumen when an external fluid is injected into the lumen from the proximal port. The valves are configured to open when the pressure of the body fluids outside of the catheter body are greater than the pressure within the lumen. In this manner, body fluids will freely flow into the lumen for heating or cooling until a fluid is injected into the lumen from outside of the patient to close the valves. In one particular aspect, the valves comprise flaps that are attached to the luminal wall and will remain open due to the pressure exerted by the body fluid until an external fluid is injected into the lumen.

The temperature altering mechanism may be configured in a variety of ways. For example, the temperature altering mechanism may comprise a resistive heater employing either electrical or radio frequency current. Various chemicals may also be employed to heat or cool the luminal wall. Alternatively, laser energy may be employed to regulate the temperature of the catheter body. In one particularly preferable aspect, the temperature altering mechanism comprises a first path which is adjacent the luminal surface and a second path which is adjacent an outer surface of the catheter body. In this way, a heat transfer fluid may be introduced into a heat transfer fluid port where it will flow through the first fluid path adjacent the luminal wall. As the heat transfer fluid flows through the first path, heat is transferred to or from the fluid flowing within the lumen. The heat transfer fluid is then circulated through the second path where it will exit the catheter body outside of the patient.

The invention further provides an exemplary method for altering the temperature of a liquid medium while the liquid medium is within a patient. According to the method, a catheter is provided having a catheter body with a proximal end and a distal end. At least one lumen extends between the proximal end and the distal end, and an internal temperature altering region is provided. The temperature altering region may be located anywhere between the proximal end and the distal end, and in some cases will preferably be located near the distal end. With this configuration, the catheter is introduced into a body structure until the temperature altering region is near a target area within the body structure. A liquid medium is introduced into the lumen, and the temperature of the liquid medium is altered while passing through the temperature altering region. In this way, the temperature of the liquid medium is altered when delivered to the target area.

In one exemplary aspect, the catheter is configured such that the liquid medium may be introduced to the lumen at the proximal end or introduced into the lumen through orifices disposed within the catheter body near the temperature altering region. In this way, a liquid medium may be introduced into the lumen from outside the patient while body fluids may also be introduced into the lumen by perfusing through the orifices. This allows various fluids, such as solutes, drugs, blood substitutes and the like to be externally injected into the catheter and then be heated or cooled before reaching the target location. Further, various body fluids, such as blood, may be heated or cooled while within the patient.

In one exemplary aspect, the method provides for preventing the body fluids from entering into the lumen while a liquid medium is externally introduced into the lumen. Following the introduction of the external liquid medium, the method provides for allowing body fluids to again enter into the orifices where they pass through the temperature altering region.

Configuration of the catheter in this manner allows for the performance of various medical procedures. For example, the distal end of the catheter may be positioned near a target site where a drug or solute is to be introduced. Inclusion of the temperature altering region allows for the drug or solute to be heated or cooled to a desired temperature upon delivery. Other fluids may also be introduced to the temperature altering region to regulate the temperature of a particular location within a body structure prior to performing a surgical procedure. For example, such a method may be employed to cool a particular vessel within the brain. Inclusion of the orifices also allows for convenient temperature regulation of the patient's blood so that a patient suffering from either hypothermia or hyperthermia may be treated.

In one exemplary aspect, the temperature of the liquid medium is altered without substantial alteration of the temperature of an outside surface of the catheter body. In another aspect, the temperature of the liquid medium is preferably heated by a temperature in the range from about 38° C. to about 40° C. In a further aspect, the temperature of a liquid medium will preferably be cooled by a temperature that is in the range from about 36° C. to about 30° C.

DESCRIPTION OF THE SPECIFIC EMBODIMENTS

The invention provides methods and apparatus for regulating the temperature of a fluid that is to be delivered to a target location within a body structure while the fluid is within the patient. The regulation of the fluid's temperature in this manner lends itself to a variety of applications including heating or cooling the temperature of a drug or solute before its delivery to a target site. Regulation of the temperature of the injected fluid may also find use in regulating the temperature of the target location itself in preparation for various medical procedures, including neurosurgical procedures within the brain. Further, the methods and apparatus allow for a patient's body temperature to be controlled by warming or cooling the patient's blood in situ. By warming or cooling the patient's blood, the patient's body temperature may thereby be increased or decreased as desired. Such methods and apparatus therefore provide a convenient therapy for treating hypothermia or hyperthermia.

Figure 1:
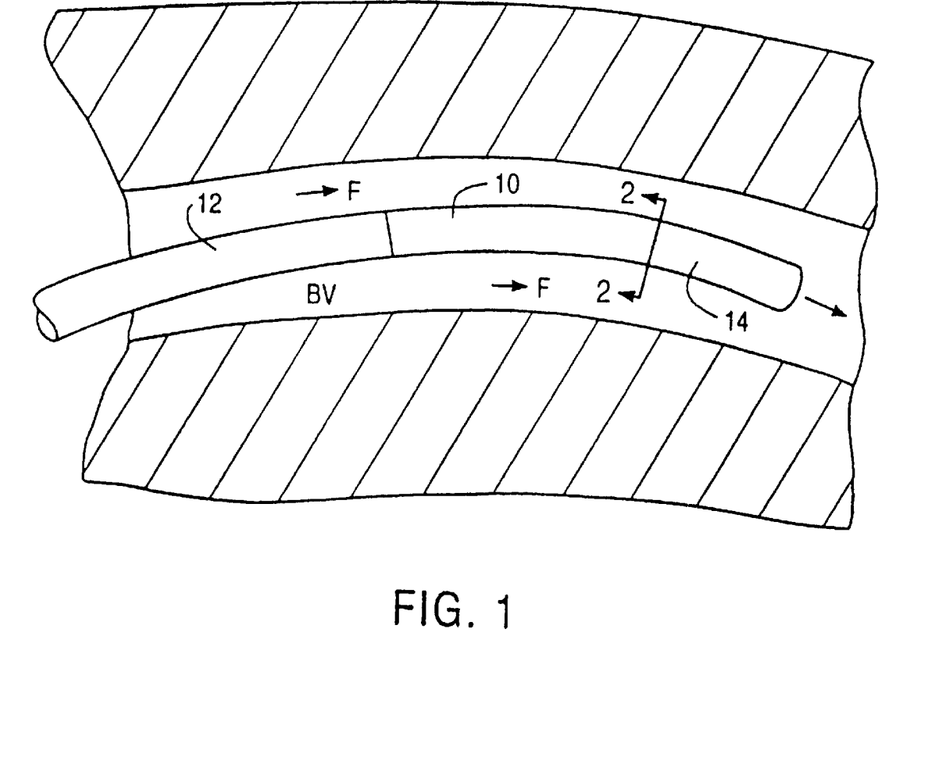
FIG. 1 depicts a distal end of a catheter according to the present invention which is inserted into a vessel of a patient.

FIG. 1 depicts a distal end 10 of a catheter 12 according to the present invention. The catheter 12 has been inserted through the patient's skin into a blood vessel BV. Blood flow through the vessel is indicated by a set of arrows F. At distal end 10 is a temperature altering region 14, it being appreciated that the temperature altering region may be located anywhere between the proximal end and the distal end.

Figure 2:
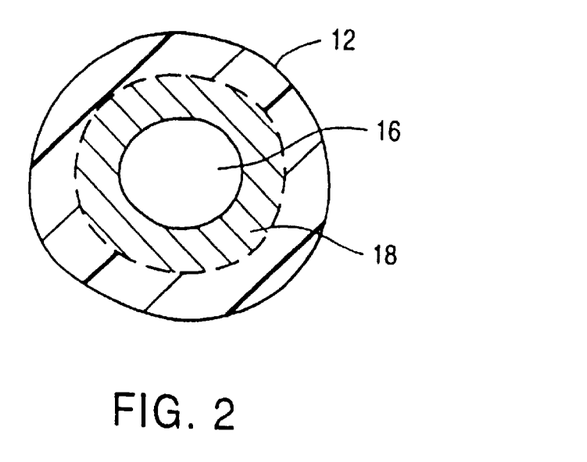
FIG. 2 is a cross-sectional side view of the catheter of FIG. 1 taken along lines 2—2 and depicting a temperature altering region.

As best shown in FIG. 2, catheter 12 includes an internal lumen 16. A temperature altering mechanism 18 is provided adjacent the luminal wall of lumen 16 at the temperature altering region 14. For convenience of discussion, temperature altering mechanism 18 is illustrated schematically and may comprise a variety of mechanisms that are employed to either heat or cool the luminal wall of lumen 16 to heat or cool the fluid passing through lumen 16 at the temperature altering region 14. Exemplary mechanisms for heating or cooling the luminal wall include heated or cooled fluids passing through catheter 12 near the luminal wall, resistive elements disposed within catheter 12, laser energy that is supplied to the temperature altering region, various chemicals disposed within the catheter body, thermoelectric crystal, and the like. Use of such mechanisms allow fluids passing through lumen 16 at the temperature altering region 14 to have their temperature altered so that they will be within a desired range when exiting catheter 12.

Catheter 12 may be manufactured in various sizes depending upon the particular application. For most uses, it will have a length in the range from about 30 cm to about 130 cm and a diameter in the range from 6 to 12 French (1 French=0.33 mm). Catheter 12 will preferably be flexible to allow the catheter to be moved through various vessels within a patient, preferably with the assistance of a guidewire.

Techniques for inserting catheters into various blood vessels are well known among medical personnel. Although the method of the present invention will probably be most commonly employed in a hospital, the procedure need not be performed in a operating room. The apparatus and procedures are so simple that the catheter may be inserted and treatment may begin in some cases even in an ambulance or in the field.

Temperature altering mechanism 18 will preferably be configured to heat a fluid passing through the temperature altering region so that its temperature will be heated by at least 5° C. to about 42° C. When cooling a fluid, the temperature altering mechanism 18 will preferably be configured to cool the fluid by at least 7° C. to about 30° C. Temperature altering mechanism 18 should be designed to optimize the rate of heat transfer between the catheter and a fluid flowing through the internal lumen. Further, the temperature of the catheter should be carefully controlled to prevent undesirable chemical changes within the blood. This is especially important when applying heat to the blood as blood is readily denatured by even moderately high temperatures. The temperature of the luminal wall for warming blood should generally not exceed about 42° C. to 43° C. The amount of energy to be supplied to heat a patient's core body temperature is described in U.S. Pat. No. 5,486,208, previously incorporated by reference.

The temperature altering mechanism 18 will preferably be arranged within catheter 12 so that the temperature of the luminal wall may be heated or cooled without substantial direct heating of an outer surface of the catheter 12. In this way, catheter 12 may be employed to selectively heat or cool a specific target site by simply positioning the distal end of the catheter at the target site and introducing a fluid through lumen 16.

Figure 3:
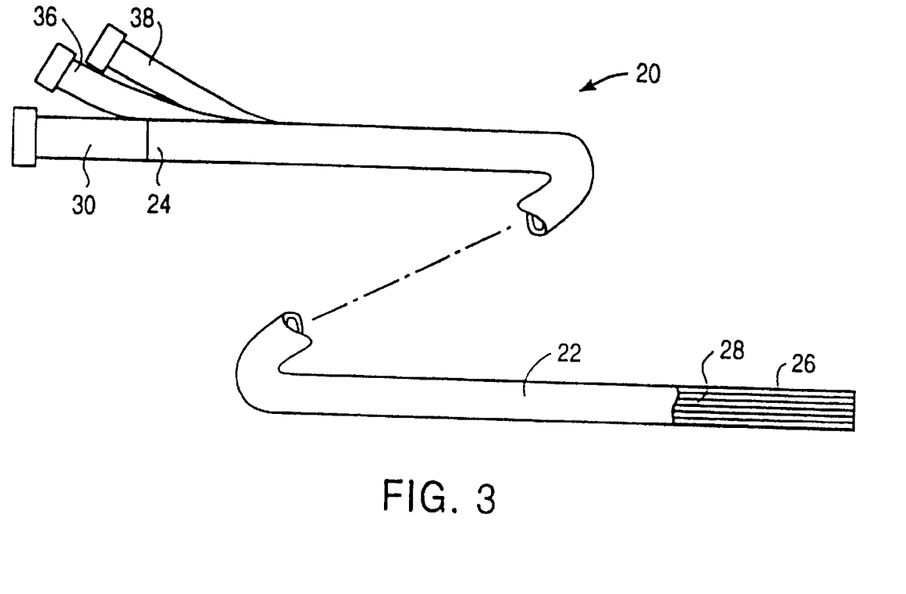
FIG. 3 is a side view of an exemplary catheter for heating or cooling a fluid passing through an internal lumen according to the invention.
Figure 4:
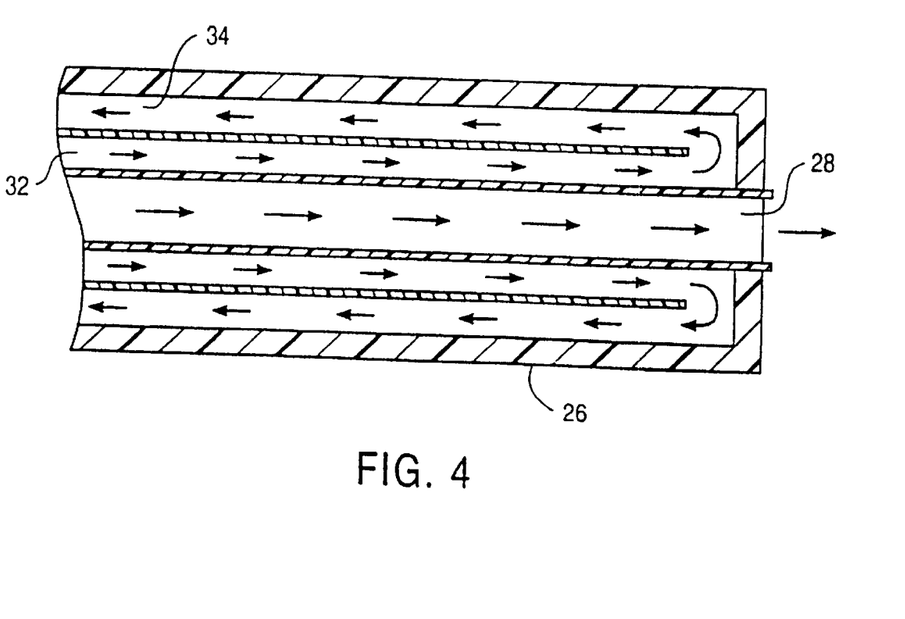
FIG. 4 is a more detailed view of a distal end the catheter of FIG. 3.

Referring now to FIG. 3, an exemplary embodiment of a catheter 20 which circulates a heat transfer fluid to alter the temperature of a fluid passing through the catheter will be described. Catheter 20 comprises a catheter body 22 having a proximal end 24 and a distal end 26. A lumen 28 extends between proximal end 24 and distal end 26. At proximal end 24 is a proximal port 30 through which various fluids may be introduced into lumen 28 from outside of a patient. Passing through catheter body 22 is a first fluid path 32 and a second fluid path 34. A first port 36 is in communication with first fluid path 32 and a second port 38 is in communication with second fluid path 34. In this manner, a heated or cooled heat transfer fluid may be introduced into first port 36 where it passes through first fluid path 32 adjacent lumen 28. As the heat transfer fluid passes through first fluid path 32, heat is transferred either to or from a fluid passing through lumen 28 to heat or cool the fluid to a desired temperature before exiting catheter body 22. After passing through first fluid path 32, the heat transfer fluid circulates back through catheter body 22 through second fluid path 34 where it exits second port 38.

Figure 5:
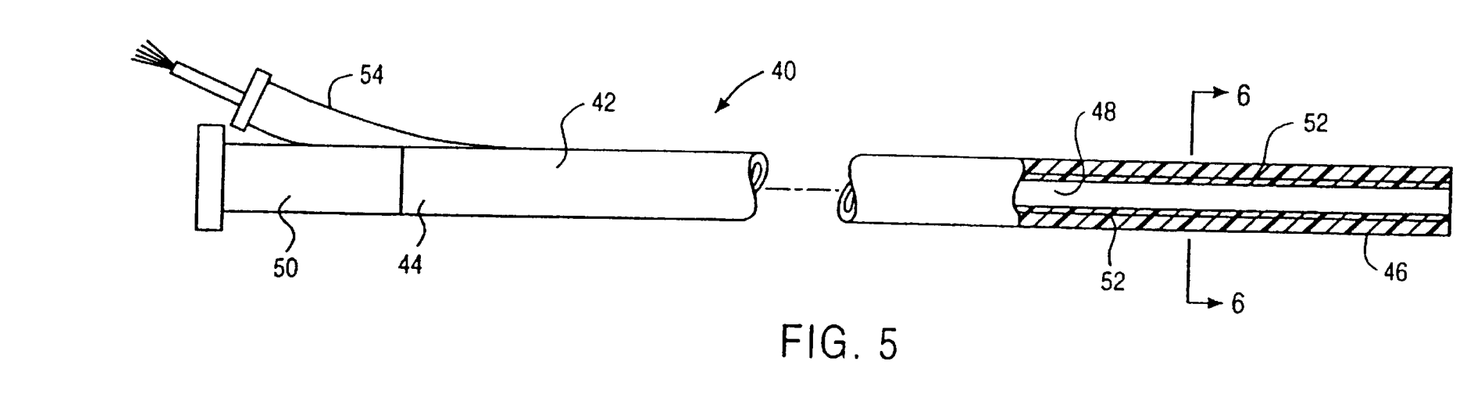
FIG. 5 is a side view of an alternative catheter for heating a fluid passing through an internal lumen according to the invention.
Figure 6:
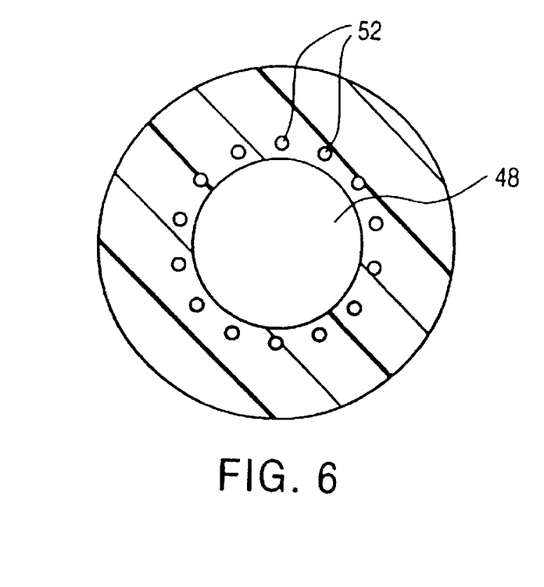
FIG. 6 is a side view of the catheter of FIG. 5 taken along lines 6—6.

FIG. 5 depicts an embodiment of a catheter 40 which employs resistive heating to heat a fluid passing through the catheter. Catheter 40 comprises a catheter body 42 having a proximal end 44 and a distal end 46. A lumen 48 passes through catheter body 42 between proximal end 44 and distal end 46. A proximal port 50 is provided to facilitate the introduction of fluids into lumen 48 from outside a patient. Disposed within catheter body 42 near lumen 48 are a plurality of wires 52 (See also FIG. 6). Wires 52 exit catheter body 42 through a port 54. Wires 52 may be connected to either a DC or low frequency AC power supply. As electrical current passes through wires 52, some of the energy is dissipated as heat to heat the luminal wall. Alternatively, a radio frequency or RF power supply may be employed to supply power to electrodes disposed within catheter body 42 to heat the luminal wall.

Figure 7:
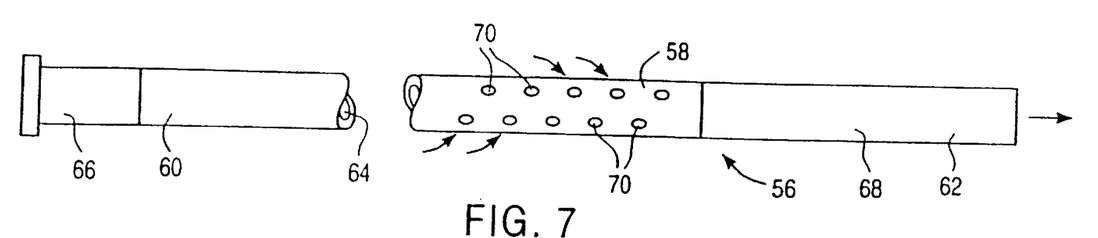
FIG. 7 is a side view of another alternative embodiment of a catheter for heating or cooling a fluid passing through an internal lumen and having a plurality of perfusion orifices for allowing body fluids to enter into the internal lumen according to the invention.
Figure 9:
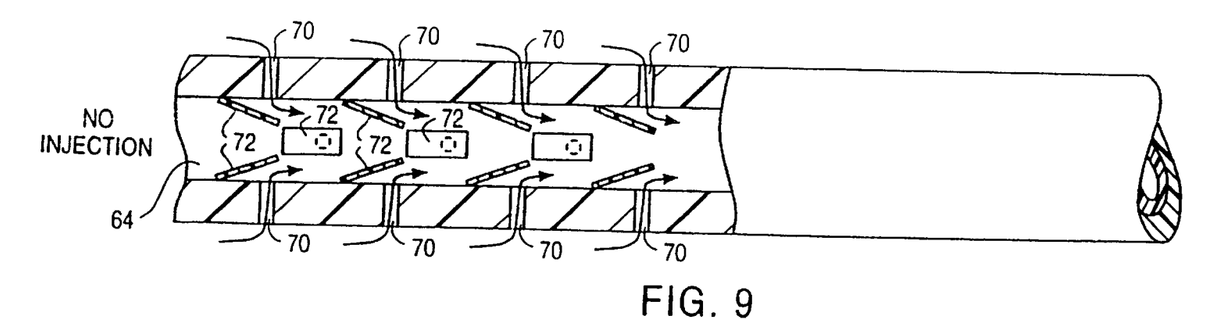
FIG. 9 illustrates the catheter of FIG. 8 showing the flaps opening to allow body fluids to enter into the internal lumen when no fluids are externally injected into the lumen.

Referring now to FIGS. 7 and 9, an exemplary embodiment of a catheter 56 which may be employed to heat or cool an externally injected fluid, to heat or cool a body fluid in situ, or both. Catheter 56 comprises a catheter body 58 having a proximal end 60 and a distal end 62. Extending between proximal end 60 and distal end 62 is a lumen 64. A proximal port 66 is provided at proximal end 60 and allows various fluids to be injected into lumen 64 while port 66 is positioned outside a patient. At distal end 62 is a temperature altering region 68 which includes a temperature altering mechanism 18. The particular temperature altering mechanism 18 may comprise any of those previously described with the other embodiments set forth herein. In this manner, a fluid which is injected into port 66 will pass through lumen 64 and have its temperature altered when passing through temperature altering region 68 in a manner similar to that previously described with other embodiments.

Catheter body 58 includes a plurality of perfusion orifices 70 which extend through the wall of the catheter body to provide fluid paths to lumen 64. As shown by the arrows in FIG. 7, a body fluid, such as blood, may pass through orifices 70 and into lumen 64 where it will have its temperature altered at region 68 so that the temperature of the body fluid will be within a desired range when exiting catheter body 58 at distal end 62 as shown.

Figure 8:
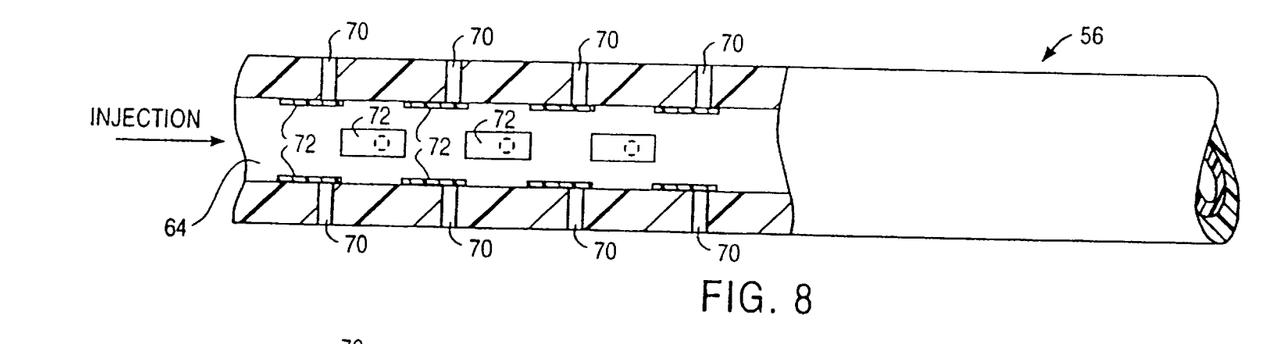
FIG. 8 is a cutaway side view of a portion of the catheter of FIG. 7 showing a plurality of flaps which are closed to prevent body fluids from entering into the internal lumen when a liquid is externally injected into the lumen.

As best shown in FIGS. 8 and 9, attached to the luminal wall of catheter body 58 are a plurality of flaps 72. Flaps 72 are employed to control the passage of body fluids through orifices 70 and into lumen 64. Flaps 72 may be constructed to be similar to those described in U.S. Pat. No. 5,180,364, the disclosure of which is herein incorporated by reference. As shown in FIG. 8, when a fluid is injected into lumen 64 at port 66, the pressure and direction of flow of the injected fluid will cause flaps 72 to close over orifices 70 so that essentially only the injected fluid will pass through temperature altering region 68. In this way, the temperature of the injected fluid will have its temperature altered so that it will be within a desired range when exiting the distal end.

As shown in FIG. 9, when no fluids are injected into port 66, the pressure of the body fluid within a vessel will cause flaps 72 to open to allow the body fluids to flow through orifices 70 and into lumen 64. In this manner, a body fluid, such as blood, may have its temperature altered by passing through orifices 70 and through temperature altering region 68. The configuration of flaps 72 in this manner is advantageous in applications where the patient's core body temperature needs to be altered. By simply introducing catheter 56 into the patient, the blood which flows into lumen 64 via orifices 70 will have its temperature altered by the time it exits distal end 62. In the event that a solute or drug is also needed for therapy, it may be introduced into lumen 64 through port 66 and have its temperature be substantially the same as the exiting blood temperature.

Figure 10:
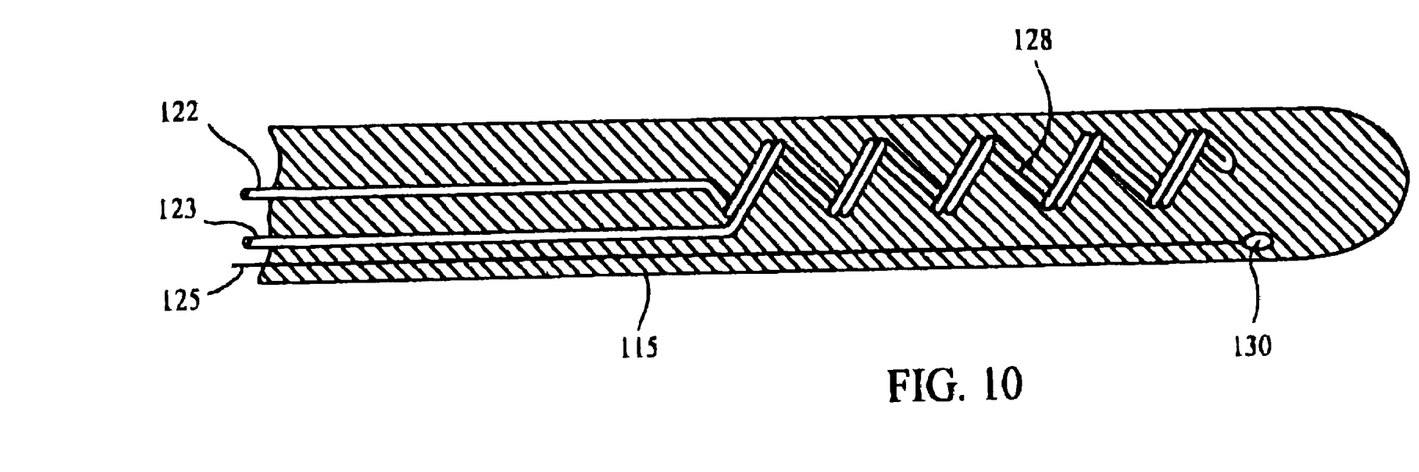
FIG. 10 depicts the distal end of a catheter having a resistance heating element and a temperature sensor.

Electrical conduction leads 122 and 123 are connected to a resistance heating element 128 as depicted in FIG. 10. Electrical current provided by a power source (not shown) is converted to heat within the heating coil. That heat warms distal end 115 of the catheter and is thereby transferred to blood flowing through the vessel. Temperature measurement lead 125 is connected to a temperature sensor 130. The temperature sensor facilitates the control of current flow through the heating coil. It is important to closely monitor the temperature of the distal end of the catheter and thus the flow of heat in,to the patient's blood. Care must be taken not to overheat the blood while still providing an adequate rate of heat transfer into the patient. The provision of a sensitive temperature sensor at the distal end of the catheter will help to achieve this goal.

Figure 11:
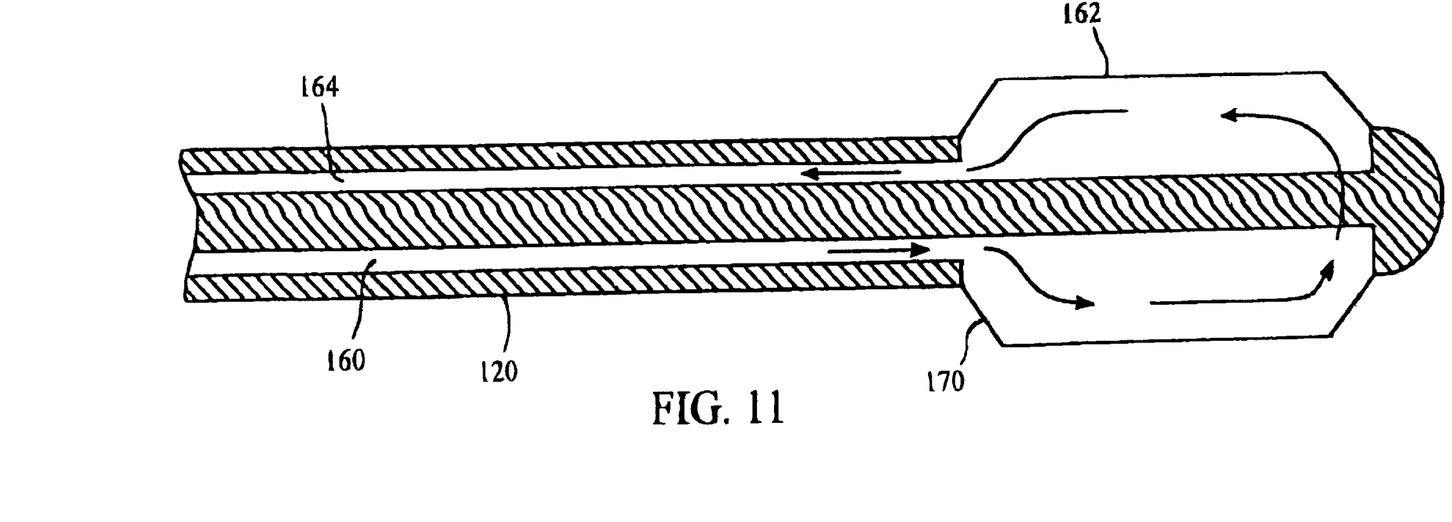
FIG. 11 depicts a catheter in which a heated or cooled fluid flows through a balloon, which provides for an increased surface area at the distal end.

FIG. 11 depicts still another means for transferring heat to or from the distal end of a catheter. In this embodiment, catheter body 120 has two lumens running through it. Fluid flows from the proximal end of the catheter through in-flow lumen 160, through a heat transfer region 162, and back out through out-flow lumen 164. By supplying either warmed or cooled fluid through inflow lumen 160, heat may be transferred either to or from the patient's blood stream. In the embodiment depicted, heat transfer region 162 is in the form of a balloon 170. Use of a balloon will be advantageous in some embodiments to provide an increased surface area through which heat transfer may take place. Balloon inflation is maintained by a pressure difference in the fluid as it flows through in-flow lumen 161) and out-flow lumen 164. The balloon should be inflated to a diameter somewhat less than that of the inside diameter of the blood vessel so as not to unduly impede the flow of blood through the vessel.

Hence, the present invention provides methods and apparatus which are useful in regulating the temperature of various fluids while such fluids are within a patent. With such an arrangement, a variety of procedures may be performed. For example, a drug or solute that is introduced from outside the patient may have its temperature altered within the catheter before reaching a target location. Further, a fluid may be heated or cooled within the catheter to in turn heat or cool a specific region of a body structure prior to the performance of a medical procedure. In another alternative, the temperature of a patient's body fluid, such as blood, may be altered in situ to treat a patient suffering from either hypothermia or hyperthermia. Although several illustrated examples of means for practicing the invention are described above, these examples are by no means exhaustive of all possible means for practicing the invention. The scope of the invention should therefore be determined with reference to the appended claims, along with a full range of equivalents to which those claims are entitled.

What is claimed is:

1. A catheter for placement in a body structure within a patient, the catheter comprising:

a catheter body having a proximal end, a distal end, at least one lumen defined by a luminal wall extending between the proximal end and the distal end said luminal wall defining at least one orifice therethrough to permit a body fluid to flow therethrough from the body of the patient into said lumen; and a temperature altering mechanism in thermal communication with said lumen which alters the temperature of the body fluid passing through the lumen.

2. A catheter as in claim 1, further comprising a proximal port at the proximal end of the catheter body which is in fluid communication with the lumen, whereby fluids introduced into the proximal port may pass through the lumen and have their temperature altered before exiting from the distal end.

3. A catheter as in claim 2, further comprising a one-way valve associated with each orifice wherein the valves prevent body fluids from entering the lumen through the at least one orifice when closed and wherein the valves are configured to close when introducing an injection fluid into the lumen from the proximal port.

4. A catheter as in claim 3, wherein the valves are configured to open when the pressure of the body fluids outside the catheter body is greater than the pressure within the lumen.

5. A catheter as in claim 4, wherein the valves comprise flaps attached to the luminal wall.

6. A catheter as in claim 1, wherein the temperature altering mechanism comprises a channel within the catheter body running parallel to at least a portion of the lumen through which a heat transfer fluid may be passed.

7. A catheter as in 6, wherein the channel includes a first path which is adjacent the luminal surface and a second path which is adjacent an outer surface of the catheter body.

8. A catheter as in claim 7, further comprising a heat transfer fluid port in communication with the first path and an exit port in communication with the second path.

9. A catheter as in claim 1, wherein the temperature altering mechanism comprises a heater.

10. A catheter as in claim 1, wherein the temperature altering mechanism comprises a cooler.

11. A catheter as in claim 1, wherein the catheter body is defined by an outer surface and the temperature altering mechanism is disposed near a luminal wall section within the temperature altering region to heat or cool the luminal wall section without substantial heating or cooling of the outer surface of the catheter body.

12. A catheter as in claim 1, wherein the catheter body is flexible and has a length in the range from about 30 cm to about 130 cm and an outer diameter in the range from about 2 mm to about 6 mm.

13. A catheter as in claim 1 wherein the catheter body has a discrete temperature altering region for heat transfer formed along only a portion of the catheter body, and further wherein said temperature altering mechanism is contained within said temperature altering region.

14. A catheter as in claim 1 wherein said body structure is a blood vessel and said body fluid is blood.

15. A heat exchange catheter comprising:
   a catheter body defined by a proximal end, a distal end, and an internal lumen defined by a luminal wall extending along at least a portion of the catheter body for passage of fluid, said catheter body is formed with at least one orifice in communication with the internal lumen to permit a body fluid to flow therethrough from the body of the patient into the internal lumen; and
   a heat transfer region defined along only a discrete portion of the catheter body distal to the proximal end of the catheter body having a temperature altering mechanism adjacent to the luminal wall of the catheter body for exchanging heat with the fluid within the lumen.

16. The heat exchange catheter as recited in claim 15 wherein the temperature altering mechanism includes a first fluid path and a second fluid path for circulating a heat transfer fluid to heat or cool fluid passing through the internal lumen of the catheter body.

17. The heat exchange catheter as recited in claim 15 wherein the catheter body is formed with a proximal port towards the proximal end of the catheter body in fluid communication with the internal lumen of the catheter body.

18. A method for regulating the temperature of a liquid medium while the liquid medium is within a patient, the method comprising:
   providing a catheter comprising a catheter body having a proximal end, a distal end, at least one lumen defined by a luminal wall extending between the proximal end and the distal end, and an internal temperature altering region disposed along the luminal wall of the catheter body for heat transfer defined by only a portion of the catheter body;
   introducing the catheter into a body structure until the distal end of the catheter body is near a target area within the body structure;
   introducing a liquid medium into the lumen; and
   altering the temperature of the liquid medium while passing through the temperature altering region so that the temperature of the liquid medium is altered when delivered to the target area.

19. A method as in claim 18, wherein the catheter body is formed with at least one orifice proximal of the temperature altering region and the liquid medium is introduced into the lumen through the at least one orifice while the at least one orifice is within the body structure.

20. A method as in claim 19, further comprising introducing an injection fluid into the lumen from the proximal end, and introducing a body fluid into the lumen through the at least one orifice while the at least one orifice is within the body structure.

21. A method as in claim 20, further comprising preventing the body fluid from entering into the lumen through the at least one orifice when the injection fluid is introduced into the lumen from the proximal end.

22. A method as in claim 21, further comprising preventing the injection fluid from exiting the catheter body through the at least one orifice, wherein the injection fluid passes through the temperature altering region and exits the catheter body from the distal end.

23. A method as in claim 18, wherein the body structure comprises a vessel.

24. A method as in claim 23, wherein the vessel is located within the brain or other organ.

25. A method as in claim 18, wherein the temperature of the liquid medium is altered without substantial alteration of the temperature of an outside surface of the catheter body.

26. A method as in claim 18, wherein the temperature of the liquid medium is heated by a temperature in the range from about 36° C. to about 42° C.

27. A method as in claim 18, wherein the temperature of the liquid medium is cooled by a temperature in the range from about 36° C. to about 30° C.

28. A method as in claim 18, wherein the liquid medium comprises a body fluid which is selected from the group of liquid mediums comprising solutes, drugs, body fluids, and blood or blood substitutes.

29. A method as in claim 18, wherein the liquid medium is introduced into the lumen at the proximal end.

30. A method as in claim 18, wherein the catheter body includes a channel and the temperature altering step further comprises passing a heat transfer fluid through the channel.

31. A method for altering the temperature of a body fluid, said method comprising the steps of:
   providing a catheter having a lumen, said lumen having at least one orifice to permit a body fluid to flow through said orifice into said lumen, said catheter further having a heat altering mechanism in thermal communication with fluid contained within said lumen;
   placing said catheter in a body structure containing body fluid;
   permitting said body fluid to enter said lumen; and
   altering the temperature of said body fluid by said heat altering mechanism.

32. A method as recited in claim 31 wherein said body structure is a blood vessel and said body fluid is blood.

* * * * *